United States Patent
Kono (10) Patent No.: US 11,730,354 B2
(45) Date of Patent: Aug. 22, 2023

(54) LIGHT SOURCE CONTROL DEVICE, MEDICAL OBSERVATION SYSTEM, LIGHT SOURCE CONTROL METHOD, AND COMPUTER READABLE RECORDING MEDIUM

(71) Applicant: Sony Olympus Medical Solutions Inc., Tokyo (JP)

(72) Inventor: Hidetaro Kono, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 219 days.

(21) Appl. No.: 16/905,927

(22) Filed: Jun. 19, 2020

(65) Prior Publication Data
US 2020/0405141 A1  Dec. 31, 2020

(30) Foreign Application Priority Data
Jun. 28, 2019 (JP) .............................. JP2019-122381

(51) Int. Cl.
*A61B 1/267* (2006.01)
*G01H 17/00* (2006.01)
*A61B 1/00* (2006.01)
*A61B 1/06* (2006.01)

(52) U.S. Cl.
CPC .......... *A61B 1/2673* (2013.01); *A61B 1/0004* (2022.02); *A61B 1/000095* (2022.02); *A61B 1/0655* (2022.02); *G01H 17/00* (2013.01)

(58) Field of Classification Search
CPC .......................................... A61B 1/267–2676
See application file for complete search history.

(56) References Cited

U.S. PATENT DOCUMENTS

| | | | | |
|---|---|---|---|---|
| 4,273,959 A | * | 6/1981 | Tuda | H05B 41/34 704/276 |
| 4,616,636 A | * | 10/1986 | Nagashima | H05B 41/34 600/249 |
| 4,782,386 A | * | 11/1988 | Ams | H05B 41/34 348/371 |
| 11,266,305 B2 | * | 3/2022 | Wichern | A61B 1/0661 |

(Continued)

FOREIGN PATENT DOCUMENTS

| | | |
|---|---|---|
| JP | 2002172088 A | 6/2002 |
| JP | 5948512 B2 | 7/2016 |
| WO | WO-2015194415 A1 | 12/2015 |

*Primary Examiner* — Eduardo C Robert
*Assistant Examiner* — Steven J Cotroneo
(74) *Attorney, Agent, or Firm* — Xsensus, LLP (57) ABSTRACT

A light source control device includes: a light source configured to intermittently emit pulse light; and a hardware processor configured to detect a vocal cord vibrational frequency of a subject based on a voice signal input from an external device, determine whether or not the vocal cord frequency is equal to or greater than a threshold value, and change a light emission frequency of the pulse light in one frame period based on image brightness based on an image signal when the vocal cord frequency is equal to or greater than the threshold value, and prohibit change in the light emission frequency and change the pulse width of the pulse light emitted by the light source based on the image brightness when the vocal cord frequency is not equal to or greater than the threshold value.

12 Claims, 8 Drawing Sheets

(56) References Cited

U.S. PATENT DOCUMENTS

| | | | |
|---|---|---|---|
| 2008/0232130 A1* | 9/2008 | Suda | A61B 1/045 |
| | | | 362/574 |
| 2009/0054790 A1* | 2/2009 | Czaniera | A61B 1/2673 |
| | | | 600/476 |
| 2009/0281390 A1* | 11/2009 | Qiu | A61B 5/0059 |
| | | | 600/199 |
| 2011/0018988 A1* | 1/2011 | Kazakevich | G02B 23/2484 |
| | | | 348/E7.085 |
| 2013/0113970 A1* | 5/2013 | Laser | A61B 1/2673 |
| | | | 348/308 |
| 2015/0141758 A1* | 5/2015 | Kagawa | A61B 1/0676 |
| | | | 600/178 |
| 2017/0042413 A1* | 2/2017 | Igarashi | A61B 1/00006 |
| 2017/0360287 A1* | 12/2017 | Morimoto | A61B 1/0653 |
| 2019/0142265 A1* | 5/2019 | Bos | H04N 5/2256 |
| | | | 600/188 |

\* cited by examiner

LIGHT SOURCE CONTROL DEVICE, MEDICAL OBSERVATION SYSTEM, LIGHT SOURCE CONTROL METHOD, AND COMPUTER READABLE RECORDING MEDIUM

This application claims priority from Japanese Application No. 2019-122381, filed on Jun. 28, 2019, the contents of which are incorporated by reference herein in its entirety.

BACKGROUND

The present disclosure relates to a light source control device that controls a light source emitting light, a medical observation system, a light source control method, and a computer readable recording medium.

In an endoscope system, observation of the vocal cords of a subject such as a person or an animal is sometimes performed by causing white light to be emitted intermittently. As such an endoscope system that performs observation of the vocal cords of a subject, a technique is known that performs strobe observation, in a stop state or a slow-motion state, of vocal cords that are vibrating at high speed by emitting pulse-like illumination light in synchronization with the vibrational frequency of the vocal cords. In strobe observation, the reading timing of the image sensor and the illumination timing are asynchronous, and therefore, even in cases where a period in which all the pixels may be commonly exposed is adequately secured, the illumination timing sometimes overlaps with the reading timing, the exposure amount differs between images, variations in brightness between images may not be eliminated, and maintaining image quality has not been possible.

Therefore, in Japanese Patent Publication No. 5948512, image quality may be maintained, even in cases where pulse light is emitted with any timing relative to the reading timing of an image sensor, by generating a one frame image signal, based on first pixel signals, which are one frame's worth of image signal and read out with reading timing that includes a pulse-light illumination period, and one frame's worth of second pixel signals, which are read out with reading timing after one frame of the first pixel signals, the one frame image signal being generated by synthesizing pixel signals which correspond to an overlap line among the first pixel signals and pixel signals which correspond to an overlap line among the second pixel signals, wherein an overlap line is configured by an overlap between a pulse-light illumination period and reading timing among a plurality of pixels in an image sensor.

SUMMARY

Incidentally, in strobe observation, a method of thinning the number of pulse light components is known as one example of a dimming method during observation. This method of thinning the number of pulses is confronted by the problem that, if the vocal cord frequency is a low frequency, the pulse-light light emission frequency substantially coincides with the frame rate of the image sensor, and therefore when the number of pulses is thinned, unexposed frames are generated.

However, because no consideration is paid to the method of thinning the number of pulses in Japanese Patent Publication No. 5948512 above, there is the problem that unexposed frames are generated when the vocal cord frequency is a low frequency.

If, on the other hand, the vocal cord frequency is a high frequency, a method of shortening the pulse width of the pulse light in strobe observation may be considered. However, there has been a problem in that the light emission cycle itself is very short, and hence pulse width limitations are quickly reached when restricting the light emission amount, and the light emission amount is not sufficiently reduced.

According to one aspect of the present disclosure, there is provided a light source control device including: a light source configured to intermittently emit pulse light; a memory; and a hardware processor configured to detect a vocal cord vibrational frequency of a subject based on a voice signal input from an external device, determine whether or not the vocal cord frequency is equal to or greater than a threshold value, and change a light emission frequency of the pulse light in one frame period of an image sensor of the pulse light emitted by the light source based on image brightness based on an image signal generated as a result of the image sensor capturing reflected light from an object when the pulse light is projected onto the object when the vocal cord frequency is equal to or greater than the threshold value, and prohibit change in the light emission frequency and change the pulse width of the pulse light emitted by the light source based on the image brightness when the vocal cord frequency is not equal to or greater than the threshold value.

DETAILED DESCRIPTION

Embodiments of the present disclosure will be described in detail hereinbelow in conjunction with the drawings. Note that the present disclosure is not limited to or by the following embodiments. Furthermore, the respective drawings referenced in the following description merely provide an approximate illustration of shapes, sizes, and positional relationships to an extent enabling an understanding of the content of the present disclosure. That is, the present disclosure is not limited to or by the shapes, sizes, and positional relationships illustrated in the respective drawings. Furthermore, the disclosures of the drawings are described by assigning the same reference signs to the same parts. In addition, as an example of a medical observation system according to the present disclosure, an endoscope system capable of observing vocal cords will be described.

First Embodiment

Overall Configuration of Endoscope System

Figure 1:
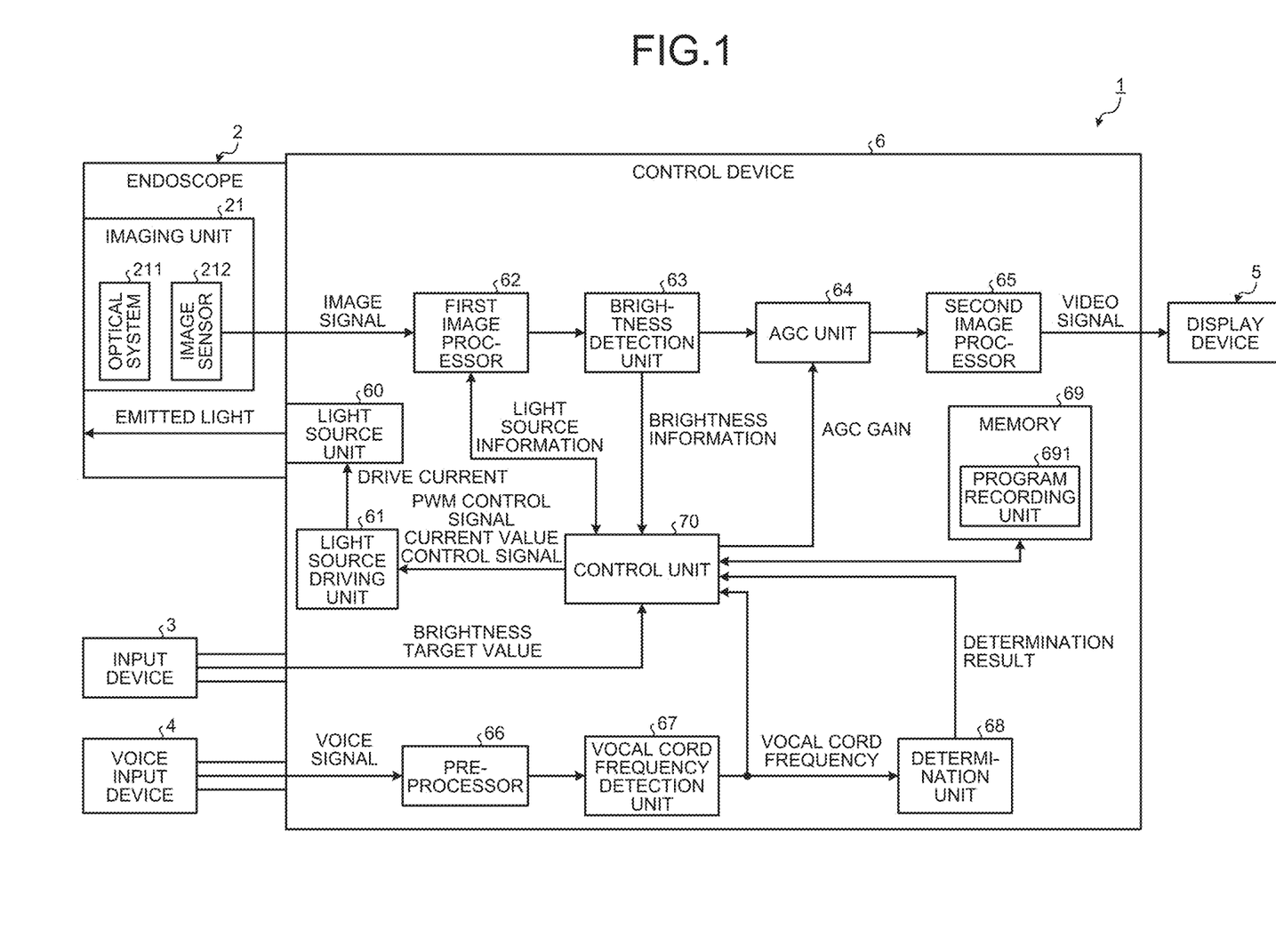
FIG. 1 is a block diagram illustrating a function configuration of an endoscope system according to a first embodiment.

FIG. 1 is a block diagram illustrating a function configuration of an endoscope system according to a first embodiment. An endoscope system 1 illustrated in FIG. 1 is used in the medical field and enables strobe observation of vocal cords serving as an object. The endoscope system 1 includes an endoscope 2, an input device 3, a voice input device 4, a display device 5, and a control device 6.

The endoscope 2 is inserted into a subject such as a living body. The endoscope 2 projects emitted light (pulse light) supplied from the control device 6, described subsequently, toward the object from the end portion of an insertable section 20, and generates an image signal for an object image by receiving light that is reflected from the object. The endoscope 2 includes an imaging unit 21 at least at the end portion of the insertable section 20.

The imaging unit 21 includes an optical system 211 and an image sensor 212. The optical system 211 includes one or a plurality of lenses and forms an object image from the object on a light-receiving surface of the image sensor 212. Based on control by the control device 6, the image sensor 212 receives the object image formed by the optical system 211 according to a predetermined frame rate and generates an image signal by photoelectrically converting the received object image. The image sensor 212 outputs the image signal to the control device 6. The image sensor 212 includes a charge coupled device (CCD) and a complementary metal oxide semiconductor (CMOS), or the like.

The input device 3 receives user operations by a user such as a doctor and outputs operation signals that correspond to the received user operations to the control device 6. The input device 3 includes a keyboard, a mouse, switches, buttons, a foot switch and a touch panel, or the like.

Based on control by the control device 6, the voice input device 4 receives inputs of voice emitted from the vocal cords and makes outputs to the control device 6 by converting this voice to a voice signal. The voice input device 4 includes a microphone or the like.

Based on control by the control device 6, the display device 5 displays a display image based on a video signal which is input from the control device 6. The display device 5 includes a display that employs liquid crystals or organic electroluminescence (EL), or the like.

The control device 6 includes at least one or more processors that include a memory and hardware such as a central processing unit (CPU), a field-programmable gate array (FPGA), and a graphics processing unit (GPU). The control device 6 integrally controls the operations of each of the parts constituting the endoscope system 1. The control device 6 includes a light source unit 60, a light source driving unit 61, a first image processor 62, a brightness detection unit 63, an autogain controller unit (called "AGC unit 64" hereinbelow), a second image processor 65, a preprocessor 66, a vocal cord frequency detection unit 67, a determination unit 68, a memory 69, and a control unit 70.

The light source unit 60 emits pulse light using a predetermined intensity and light emission period based on a drive current which is input from the light source driving unit 61. The light source unit 60 includes a white LED (light emitting diode) and a condenser lens, or the like. The pulse light emitted by the light source unit 60 is emitted toward an object from the end of the endoscope 2. Note that the light source unit 60 is not limited to a white LED and may be configured capable of emitting white light by combining light which is emitted by a red LED, a green LED, and a green LED, respectively.

Based on control by the control unit 70, the light source driving unit 61 causes the light source unit 60 to emit pulse light at a pulse-light light emission frequency in the predetermined one frame period and to emit the pulse light at a predetermined intensity. Specifically, the light source driving unit 61 causes the light source unit 60 to emit light based on a PWM control signal and a current value control signal which are input from the control unit 70.

Based on the control unit 70, the first image processor 62 performs various image processing on the image signal which is input from the image sensor 212 of the endoscope 2 and makes outputs to the brightness detection unit 63. Here, the various image processing by the first image processor 62 is, with respect to a pixel signal, A/D conversion processing, optical black subtraction processing, white balance (WB) adjustment processing, demosaic processing (in the case of a configuration in which the image sensor 212 includes a Bayer array color filter (not illustrated)), color matrix arithmetic processing, gamma correction processing, color reproduction processing, and edge enhancement processing, and the like. In addition, the first image processor 62 generates a pseudo image signal based on light source information that is input from the control unit 70 and that relates to the light emission frequency of pulse light in one frame period of the light source unit 60, the current value supplied to the light source unit 60, and the pulse width of the pulse light. Specifically, the first image processor 62 generates, from an image signal of a plurality of continuous frames, a pseudo pixel signal that corresponds to a pixel signal in a case where all the pixels of the image sensor 212 are exposed in a pulse-light light illumination period by the light source unit 60. More specifically, when generating the pseudo pixel signal, the first image processor 62 generates the pseudo pixel signal by using, for a specified horizontal line among horizontal lines of a plurality of pixels in the image sensor 212, an image signal which is obtained by multiplying a specified one frame's worth of image signal from the respective pixels of the specified horizontal line by the ratio, of a specified pulse-light exposure amount resulting from exposure in a specified one frame, to the total exposure amount obtained by adding up all of the respective pulse-light exposure amounts resulting from exposure of the specified horizontal line in one specified frame that contains a specified pulse-light illumination period.

The brightness detection unit 63 detects the brightness of an image based on an image signal or a pseudo image signal (an image signal) which is input from the first image processor 62 and outputs brightness information relating to this brightness to the control unit 70. Here, brightness information is an average value for the luminance of each pixel in the image based on the pseudo image signal or image signal. Furthermore, the brightness detection unit 63 outputs the pseudo image signal, which has been input from the first image processor 62, to the AGC unit 64.

Based on control by the control unit 70, the AGC unit 64 adjusts the gain of the pseudo image signal which is input from the brightness detection unit 63 and of the pseudo image signal which is to be output so that the gain assumes a predetermined value, and outputs the adjusted gain to the second image processor 65.

Based on control by the control unit 70, the second image processor 65 generates a video signal by performing various image processing on the pseudo image signal that has been input from the AGC unit 64 and outputs the video signal to the display device 5. For example, when the pseudo image signal is RGB data, the second image processor 65 performs image processing to convert RGB data to YUV data.

The preprocessor 66 amplifies a voice signal that has been input from the voice input device 4, performs A/D conversion processing on the amplified voice signal, and outputs the A/D converted signal to the vocal cord frequency detection unit 67. Note that the functions of the preprocessor 66 may also be provided in the voice input device 4.

Based on the voice signal that has been input from the preprocessor 66, the vocal cord frequency detection unit 67 detects the frequency of vibration of voice which is input to the voice input device 4. Specifically, the vocal cord frequency detection unit 67 detects a vocal cord vibrational frequency based on the voice signal that has been input from the preprocessor 66 and outputs the detected vibrational frequency to the control unit 70 and the determination unit 68.

The determination unit 68 determines whether or not the vocal cord frequency which has been input from the vocal cord frequency detection unit 67 is equal to or greater than a threshold value and outputs the determination result to the control unit 70. Here, the threshold value is two times the frequency of the frame rate of the image sensor 212. That is, the determination unit 68 determines whether or not the vocal cord frequency which has been input from the vocal cord frequency detection unit 67 is two or more times the frequency of the frame rate of the image sensor 212. When the vocal cord frequency (60 Hz, for example) is two (120 Hz) or more times the frequency of the frame rate of the image sensor 212, the determination unit 68 determines that the vocal cord frequency is a high frequency and outputs this determination result to the control unit 70. In contrast, when the vocal cord frequency (60 Hz, for example) is not two (120 Hz) or more times the frequency of the frame rate of the image sensor 212, the determination unit 68 determines that the vocal cord frequency is a low frequency and outputs this determination result to the control unit 70.

The memory 69 records various information and the like which is executed by the endoscope system 1. The memory 69 includes a volatile memory, a nonvolatile memory, and a removable memory card, or the like. Furthermore, the memory 69 includes a program recording unit 691 that records various programs executed by the endoscope system 1.

The control unit 70 includes at least one or more processors that include a memory and hardware such as a CPU. When it has been determined by the determination unit 68 that the vocal cord frequency is equal to or greater than a threshold value, the control unit 70 changes the pulse-light light emission frequency in one frame period when causing the light source unit 60 to emit pulse light, based on the image brightness based on the image signal or the pseudo image signal generated as a result of the image sensor 212 capturing the reflected light from an object when the light source unit 60 projects pulse light onto the object. Furthermore, when it has been determined by the determination unit 68 that the vocal cord frequency is not equal to or greater than a threshold value, the control unit 70 prohibits changes to the pulse-light light emission frequency in one frame period when causing the light source unit 60 to emit pulse light, based on the image brightness based on the image signal or the pseudo image signal generated as a result of the image sensor 212 capturing the reflected light from an object when the light source unit 60 projects pulse light onto the object, and the control unit 70 changes the pulse width when causing the light source unit 60 to emit pulse light.

Note that, in the first embodiment, the light source unit 60, the light source driving unit 61, the vocal cord frequency detection unit 67, the determination unit 68, and the control unit 70 function as a light source control device. Furthermore, in the first embodiment, the light source unit 60, the light source driving unit 61, the vocal cord frequency detection unit 67, the determination unit 68, and the control unit 70 are provided in the control device 6 but are not limited to such provision and may be provided separately. In addition, in the first embodiment, the first image processor 62, the brightness detection unit 63, the AGC unit 64, and the second image processor 65 function as an image processing device.

Endoscope System Processing

Figure 2:
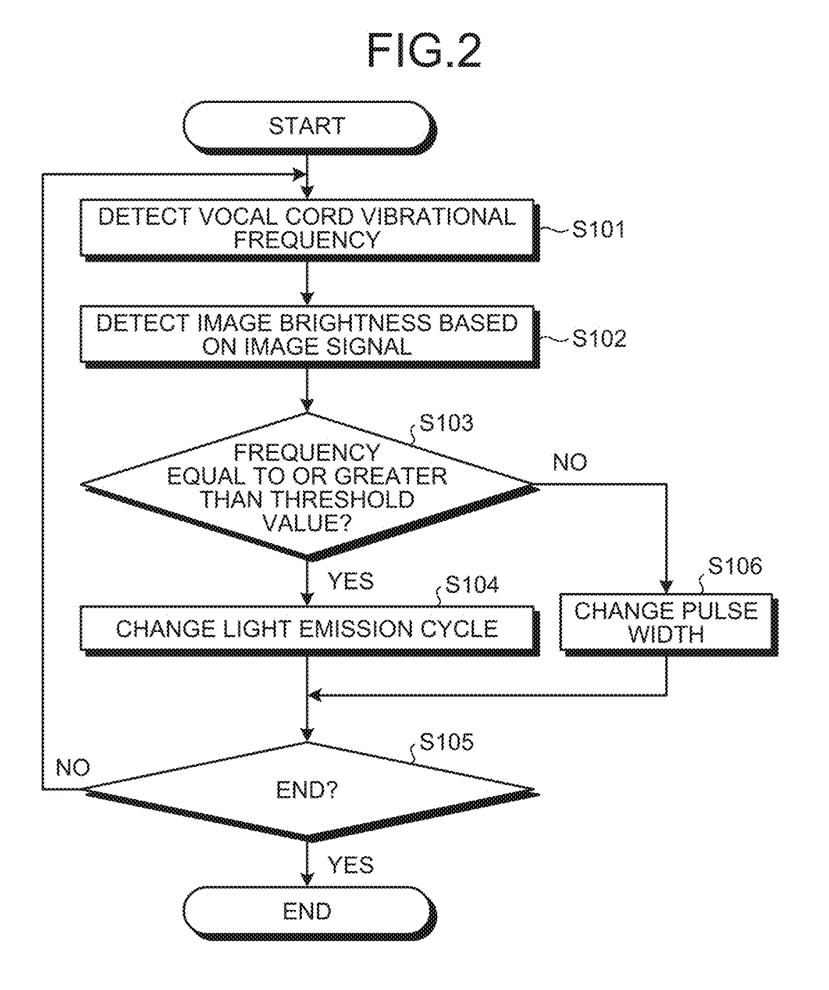
FIG. 2 is a flowchart illustrating an overview of processing executed by an endoscope system according to the first embodiment.

The processing executed by the endoscope system 1 will be described next. FIG. 2 is a flowchart illustrating an overview of processing executed by the endoscope system 1.

As illustrated in FIG. 2, the vocal cord frequency detection unit 67 first detects the vocal cord vibrational frequency based on a voice signal that is input from the voice input device 4 via the preprocessor 66 (step S101).

Next, the brightness detection unit 63 detects the image brightness based on the image signal (pseudo image signal) which has been input from the first image processor (step S102).

Thereafter, the determination unit 68 determines whether or not the vocal cord vibrational frequency which has been input from the vocal cord frequency detection unit 67 is equal to or greater than a threshold value (step S103). When it is determined by the determination unit 68 that the vocal cord vibrational frequency is equal to or greater than the threshold value (step S103: Yes), the endoscope system 1 moves to step S104, described subsequently. In contrast, when it is determined by the determination unit 68 that the vocal cord vibrational frequency is not equal to or greater than the threshold value (step S103: No), the endoscope system 1 moves to step S106, described subsequently.

In step S104, the control unit 70 changes the pulse-light light emission frequency in one frame period of the pulse light emitted by the light source unit 60, based on a target value for the image brightness which is input from the input device 3, brightness information detected by the brightness detection unit 63, and the determination result of the determination unit 68. After step S104, the endoscope system 1 moves to step S105, described subsequently.

Figure 3:
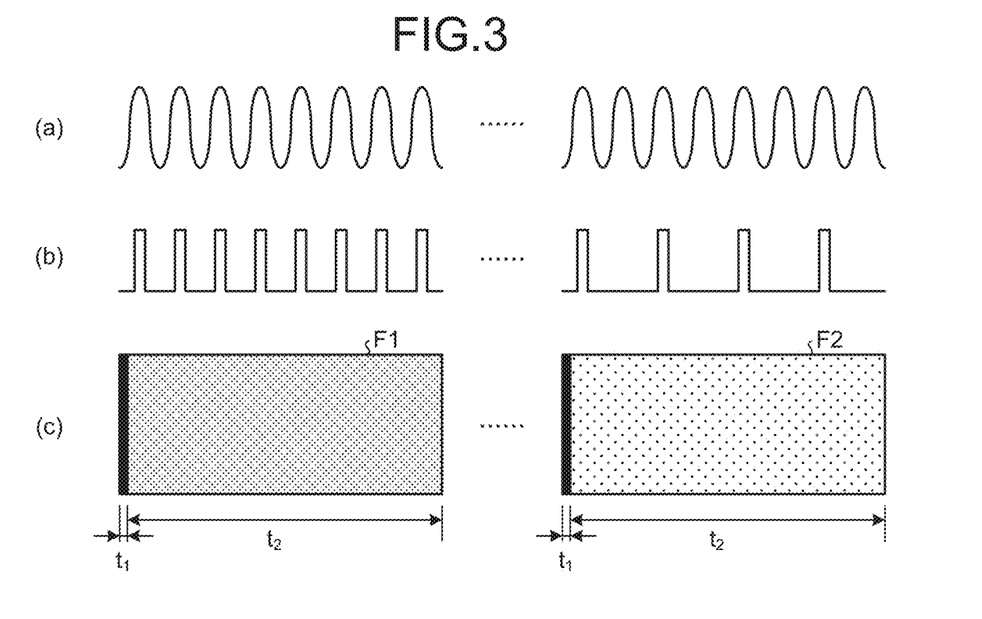
FIG. 3 is a diagram illustrating an overview of when the pulse-light light emission frequency in one frame period of a light source unit is changed by a control unit according to the first embodiment.

FIG. 3 is a diagram illustrating an overview of when the light emission period of the light source unit 60 is changed by the control unit 70. In FIG. 3, starting at the top, (a) illustrates the vocal cord vibrational frequency, (b) illustrates the light emission timing and intensity of the pulse light, and (c) illustrates exposure frames of the image sensor 212. Furthermore, the horizontal axis in (a) of FIG. 3 represents time and the vertical axis represents the phase state of vocal cord vibration, the horizontal axis in (b) of FIG. 3 represents time and the vertical axis represents intensity, the horizontal axis in (c) of FIG. 3 represents time, time $t_1$ represents timing for reading the image signal, and time $t_2$ represents exposure timing. In addition, frame F1 in (c) of FIG. 3 represents a frame (image signal) in which the image brightness is too bright, and frame F2 represents a frame (image signal) of appropriate brightness.

As illustrated in FIG. 3, the control unit 70 performs control to change the pulse-light light emission frequency in one frame period of the pulse light emitted by the light source unit 60, based on a target value for the image brightness which is input from the input device 3, brightness information detected by the brightness detection unit 63, the determination result which is input from the determination unit 68, and the vocal cord frequency which is input from the vocal cord frequency detection unit 67. Specifically, when it is determined by the determination unit 68 that the vocal cord frequency is equal to or greater than a threshold value, that is, when it is determined that the vocal cord frequency is a high frequency, the control unit 70 changes the light emission cycle (light emission frequency) by thinning the light emission frequency with which the light source unit 60 is made to emit pulse light in synchronization with the vocal cord frequency, in one frame period of the image sensor 212. More specifically, the control unit 70 outputs, to the light source driving unit 61, a PWM control signal whereby the light emission frequency at which the light source unit 60 emits pulse light is changed in one frame period to achieve a target value brightness, based on the difference between a target value for the image brightness which is input from the input device 3 and the detection result of the brightness detection unit 63. In this case, the light source driving unit 61 supplies a drive current (a pulse current) to the light source unit 60 in synchronization with a maximum value for the vocal cord vibrational frequency based on the PWM control signal and the current value control signal which are input from the control unit 70. As a result, frame F2 has an appropriate brightness.

Returning to FIG. 2, the description of step S105 and subsequent steps will now be resumed.

In S105, when an end signal to end the subject inspection has been input from the input device 3 (step S105: Yes), the endoscope system 1 ends the processing. In contrast, when an end instruction to end the subject inspection has not been input from the input device 3 (step S105: No), the endoscope system 1 returns to step S101 above.

In step S106, the control unit 70 performs control to prohibit changes to the pulse-light light emission frequency in one frame period of the pulse light emitted by the light source unit 60 and to change the pulse width of the pulse light emitted by the light source unit 60, based on a target value for the image brightness which is input from the input device 3, brightness information detected by the brightness detection unit 63, the determination result which is input from the determination unit 68, and the vocal cord frequency which is input from the vocal cord frequency detection unit 67. After step S106, the endoscope system 1 moves to step S105.

Figure 4:
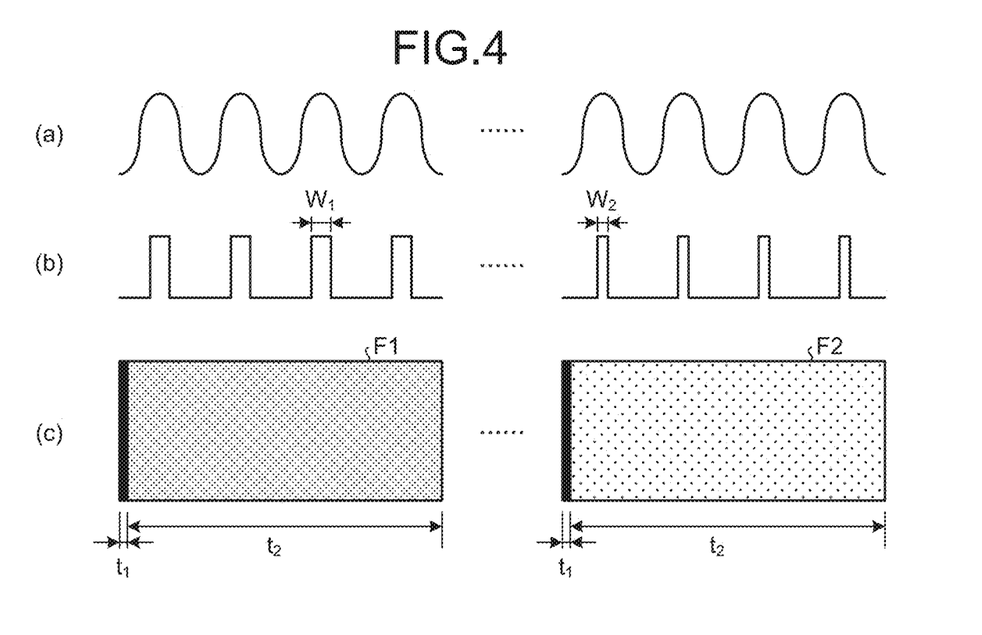
FIG. 4 is a diagram illustrating an overview of when the pulse width of the light source unit is changed by the control unit according to the first embodiment.

FIG. 4 is a diagram illustrating an overview of when the pulse width of the light source unit 60 is changed by the control unit 70. In FIG. 4, starting at the top, (a) illustrates the vocal cord vibrational frequency, (b) illustrates the light emission timing and intensity of the pulse light, and (c) illustrates exposure frames of the image sensor 212. Furthermore, the horizontal axis in (a) of FIG. 4 represents time and the vertical axis represents the phase state of vocal cord vibration, the horizontal axis in (b) of FIG. 4 represents time and the vertical axis represents intensity, the horizontal axis in (c) of FIG. 4 represents time, time $t_1$ represents timing for reading the image signal, and time $t_2$ represents exposure timing. In addition, frame F1 in (c) of FIG. 4 represents a frame (image signal) in which the image brightness is too bright, and frame F2 represents a frame (image signal) of appropriate brightness.

As illustrated in FIG. 4, the control unit 70 performs control to change the pulse width of the pulse light emitted by the light source unit 60, based on a target value for the image brightness which is input from the input device 3, brightness information detected by the brightness detection unit 63, the determination result which is input from the determination unit 68, and the vocal cord frequency which is input from the vocal cord frequency detection unit 67. Specifically, when it is determined by the determination unit 68 that the vocal cord frequency is not equal to or greater than a threshold value, that is, when it is determined that the vocal cord frequency is a low frequency, the control unit 70 changes the pulse width with which the light source unit 60 is made to emit pulse light in synchronization with the vocal cord frequency, in one frame period of the image sensor 212. More specifically, the control unit 70 outputs, to the light source driving unit 61, a PWM control signal whereby the pulse width of the pulse light emitted by the light source unit 60 is changed from a pulse width $W_1$ to a pulse width $W_2$ to achieve a target value brightness, based on the difference between a target value for the image brightness which is input from the input device 3 and the detection result of the brightness detection unit 63. In this case, the light source driving unit 61 supplies a drive current (a pulse current) of pulse width $W_2$ to the light source unit 60 in synchronization with the maximum value for the vocal cord vibrational frequency, based on the PWM control signal which is input from the control unit 70. As a result, frame F2 has an appropriate brightness.

According to the first embodiment described hereinabove, in a case where it is determined by the determination unit 68 that the vocal cord frequency is equal to or greater than the threshold value, the control unit 70 changes the pulse-light light emission frequency in one frame period of the pulse light emitted by the light source unit 60 based on image brightness based on an image signal generated by the image sensor 212, whereas, in a case where it is determined by the determination unit 68 that the vocal cord frequency is not equal to or greater than the threshold value, the control unit 70 prohibits changes to the light emission cycle when causing the light source unit 60 to emit pulse light and changes the pulse width of the pulse light emitted by the light source unit 60, based on the image brightness based on the image signal generated by the image sensor 212, and it is therefore possible to perform optimal strobe observation according to vocal cord frequency.

Furthermore, according to the first embodiment, when it is determined by the determination unit 68 that the vocal cord frequency is not equal to or greater than the threshold value, that is, when it is determined that the vocal cord frequency is not two or more times the frequency of the frame rate of the image sensor 212, the control unit 70 prohibits changes to the pulse-light light emission frequency in one frame period of the pulse light emitted by the light source unit 60 and performs dimming by changing only the pulse width of the pulse light emitted by the light source unit 60, and it is therefore possible to obtain image signal frames obtained through reliable exposure even when the vocal cord frequency is a low frequency.

Moreover, according to the first embodiment, an adequate dimming range can be secured irrespective of whether the vocal cord frequency is a low frequency or a high frequency.

Furthermore, according to the first embodiment, because the control unit 70 performs dimming by changing the pulse-light light emission frequency or the pulse width in one frame period of the pulse light emitted by the light source unit 60, it is possible to prevent color temperature changes in the image in comparison with dimming performed by changing the current value to the light source unit 60.

In addition, according to the first embodiment, an adequate dimming range may be secured even when a mechanical diaphragm mechanism is not provided separately or in the endoscope 2, and therefore not only the endoscope 2 may be manufactured inexpensively, the insertable section 20 of the endoscope 2 may also be reduced in diameter.

Note that, in the first embodiment, when the control unit 70 changes the pulse-light light emission frequency in one frame period of the pulse light emitted by the light source unit 60 in cases where it is determined by the determination unit 68 that the vocal cord frequency is equal to or greater than the threshold value, the control unit 70 changes the pulse-light light emission frequency in one frame period by thinning the initial pulse-light light emission in one frame period of the image sensor 212. However, the present embodiment is not limited to or by such an arrangement, rather, the control unit 70 may, for example, change the pulse-light light emission frequency in one frame period by thinning the initial pulse-light light emission in one frame period or may change the pulse-light light emission frequency in one frame period by thinning predetermined light emission in one frame period.

Second Embodiment

A second embodiment will be described next. The second embodiment includes the same configurations as the endoscope system 1 according to the foregoing first embodiment and the processing executed is different. Specifically, in the foregoing first embodiment, control to change the light emission frequency or pulse width of pulse light in one frame period is performed depending on whether the vocal cord vibrational frequency is equal to or greater than the threshold value, but in the second embodiment, control to change the light emission frequency or pulse width of pulse light in one frame period is performed after changing the light emission intensity of the light source unit according to an image brightness target value. The processing executed by the endoscope system according to the foregoing second embodiment will be described hereinbelow. Note that the same reference signs are assigned to the same configurations as in the endoscope system 1 according to the foregoing first embodiment and that detailed descriptions of these configurations are omitted.

Endoscope System Processing

Figure 5:
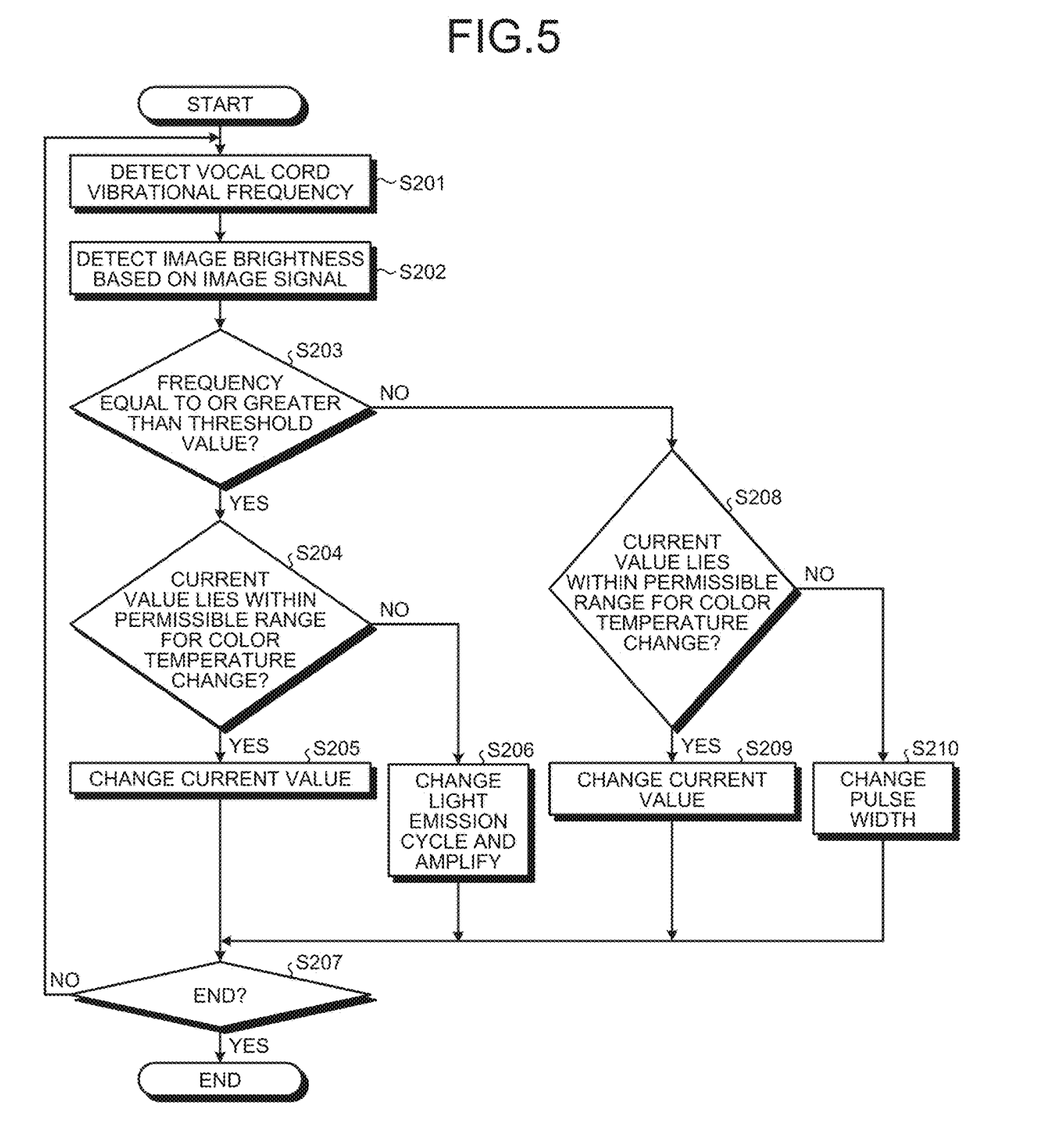
FIG. 5 is a flowchart illustrating an overview of processing executed by an endoscope system according to a second embodiment.

FIG. 5 is a flowchart illustrating an overview of processing executed by an endoscope system 1 according to the second embodiment. Steps S201 to S203 in FIG. 5 correspond to the foregoing steps S101 to S103, respectively, in FIG. 2.

In step S204, the control unit 70 determines whether or not the current value which the light source driving unit 61 supplies to the light source unit 60 lies within a permissible range for a color temperature change. When it is determined by the control unit 70 that the current value which the light source driving unit 61 supplies to the light source unit 60 lies within the permissible range for a color temperature change (step S204: Yes), the endoscope system 1 moves to step S205, described subsequently. In contrast, when it is determined by the control unit 70 that the current value which the light source driving unit 61 supplies to the light source unit 60 is not within the permissible range for a color temperature change (step S204: No), the endoscope system 1 moves to step S206, described subsequently.

In step S205, the control unit 70 changes the current value which the light source driving unit 61 supplies to the light source unit 60 based on a target value for the image brightness which is input from the input device 3, brightness information detected by the brightness detection unit 63, and the vocal cord frequency which is input from the vocal cord frequency detection unit 67. Note that details on changes to the current value by the control unit 70 will be described subsequently. After step S205, the endoscope system 1 moves to step S207, described subsequently.

In step S206, the control unit 70 performs control to change the pulse-light light emission frequency in one frame period of the pulse light emitted by the light source unit 60 after changing the current value up to the tolerance limit for color temperature changes, while causing the AGC unit 64 to amplify the image signal, based on a target value for the image brightness which is input from the input device 3, brightness information detected by the brightness detection unit 63, and the vocal cord frequency which is input from the vocal cord frequency detection unit 67. Note that the details of the control by the control unit 70 to change the pulse-light light emission frequency in one frame period while causing the AGC unit 64 to amplify the image signal will be described subsequently. After step S206, the endoscope system 1 moves to step S207, described subsequently.

Figure 6:
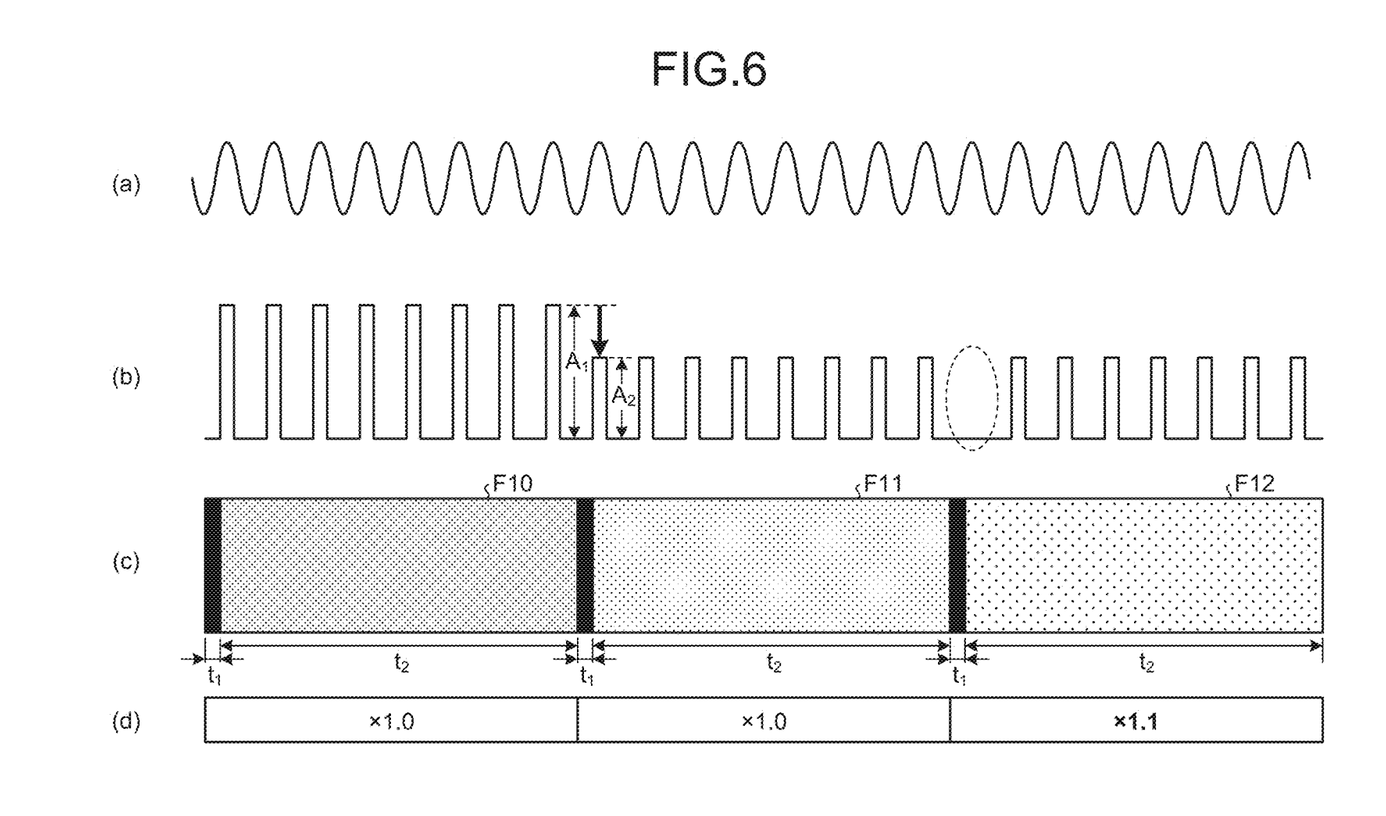
FIG. 6 is a diagram illustrating an overview of control by the control unit in a case where the vocal cord vibrational frequency is equal to or greater than a threshold value.

FIG. 6 is a diagram illustrating an overview of control by the control unit 70 in a case where the vocal cord vibrational frequency is equal to or greater than a threshold value. In FIG. 6, starting at the top, (a) illustrates the vocal cord vibrational frequency, (b) illustrates the light emission timing and intensity of the pulse light, (c) illustrates exposure frames of the image sensor 212, and (d) illustrates the gain which is applied to the image signal of the exposure frames by the AGC unit 64. Furthermore, the horizontal axis in (a) of FIG. 6 represents time and the vertical axis represents the phase state of vocal cord vibration, the horizontal axis in (b) of FIG. 6 represents time and the vertical axis represents intensity, the horizontal axis in (c) of FIG. 6 represents time, time $t_1$ represents timing for reading the image signal, and time $t_2$ represents exposure timing. In addition, frame F10 in (c) of FIG. 6 represents a frame (image signal) in which the image brightness is too bright, frame F11 represents a frame (image signal) for which a color temperature change is permissible, and frame F12 represents a frame (image signal) of appropriate brightness.

As illustrated in FIG. 6, first a case will be described where the control unit 70 controls the current value which the light source driving unit 61 supplies to the light source unit 60 to be within a permissible range (frame F11) for a color temperature change. In this case, the control unit 70 changes the light emission intensity from a light emission intensity $A_1$ to a light emission intensity $A_2$ by changing the current value which the light source driving unit 61 supplies to the light source unit 60, thereby performing dimming to the target value for the image brightness which has been input from the input device 3 (continuous dimming control). Specifically, the control unit 70 outputs, to the light source driving unit 61, a current value control signal that corresponds to the light emission intensity $A_2$ constituting the target value brightness. At such time, the light source driving unit 61 supplies a drive current (a pulse current) to the light source unit 60 in synchronization with the vocal cord vibrational frequency based on the PWM control signal and the current value control signal which are input from the control unit 70.

Thereafter, when the current value which the light source driving unit 61 supplies to the light source unit 60 is not within the permissible range for a color temperature change, the control unit 70 performs control to change the light emission cycle (light emission frequency) by thinning the light emission frequency of the pulse light emitted by the light source unit 60 in synchronization with the vocal cord frequency in one frame period of the image sensor 212, while causing the AGC unit 64 to amplify the image signal. Specifically, the control unit 70 outputs, to the light source driving unit 61, a PWM control signal to indicate thinning of an initial pulse light emission in one frame period, which constitutes a PWM control signal whereby the frequency at which the light source unit 60 emits pulse light in one frame period is changed to achieve a target value brightness, based on the difference between a target value for the image brightness which is input from the input device 3 and the detection result of the brightness detection unit 63. At such time, the light source driving unit 61 supplies a drive current (a pulse current) to the light source unit 60 in synchronization with the vocal cord vibrational frequency based on the PWM control signal and the current value control signal which are input from the control unit 70. Furthermore, the control unit 70 causes the AGC unit 64 to amplify the image signal of the latest frame F12 by 1.1 times, for example, in order to absorb discontinuity in the brightness based on control of the pulse-light light emission frequency in one frame period. As a result, frame F12 has an appropriate brightness.

Returning to FIG. 5, the description of step S207 and subsequent steps will now be resumed.

In S207, when an end signal to end the subject inspection has been input from the input device 3 (step S207: Yes), the endoscope system 1 ends the processing. In contrast, when an end instruction to end the subject inspection has not been input from the input device 3 (step S207: No), the endoscope system 1 returns to step S201 above.

In step S208, the control unit 70 determines whether or not the current value which the light source driving unit 61 supplies to the light source unit 60 is in a permissible range for a color temperature change. When it is determined by the control unit 70 that the current value which the light source driving unit 61 supplies to the light source unit 60 is in the permissible range for a color temperature change (step S208: Yes), the endoscope system 1 moves to step S209, described subsequently. In contrast, when it is determined by the control unit 70 that the current value which the light source driving unit 61 supplies to the light source unit 60 is not in the permissible range for a color temperature change (step S208: No), the endoscope system 1 moves to step S210, described subsequently.

In step S209, the control unit 70 changes the current value which the light source driving unit 61 supplies to the light source unit 60 based on a target value for the image brightness which is input from the input device 3, brightness information detected by the brightness detection unit 63, and the vocal cord frequency which is input from the vocal cord frequency detection unit 67. Note that details on changes to the current value by the control unit 70 will be described subsequently. After step S209, the endoscope system 1 moves to step S207.

In step S210, the control unit 70 changes the pulse width with which the light source unit 60 emits pulse light, based on a target value for the image brightness which is input from the input device 3, brightness information detected by the brightness detection unit 63, and the vocal cord frequency which is input from the vocal cord frequency detection unit 67. After step S207, the endoscope system 1 moves to step S207.

Figure 7:
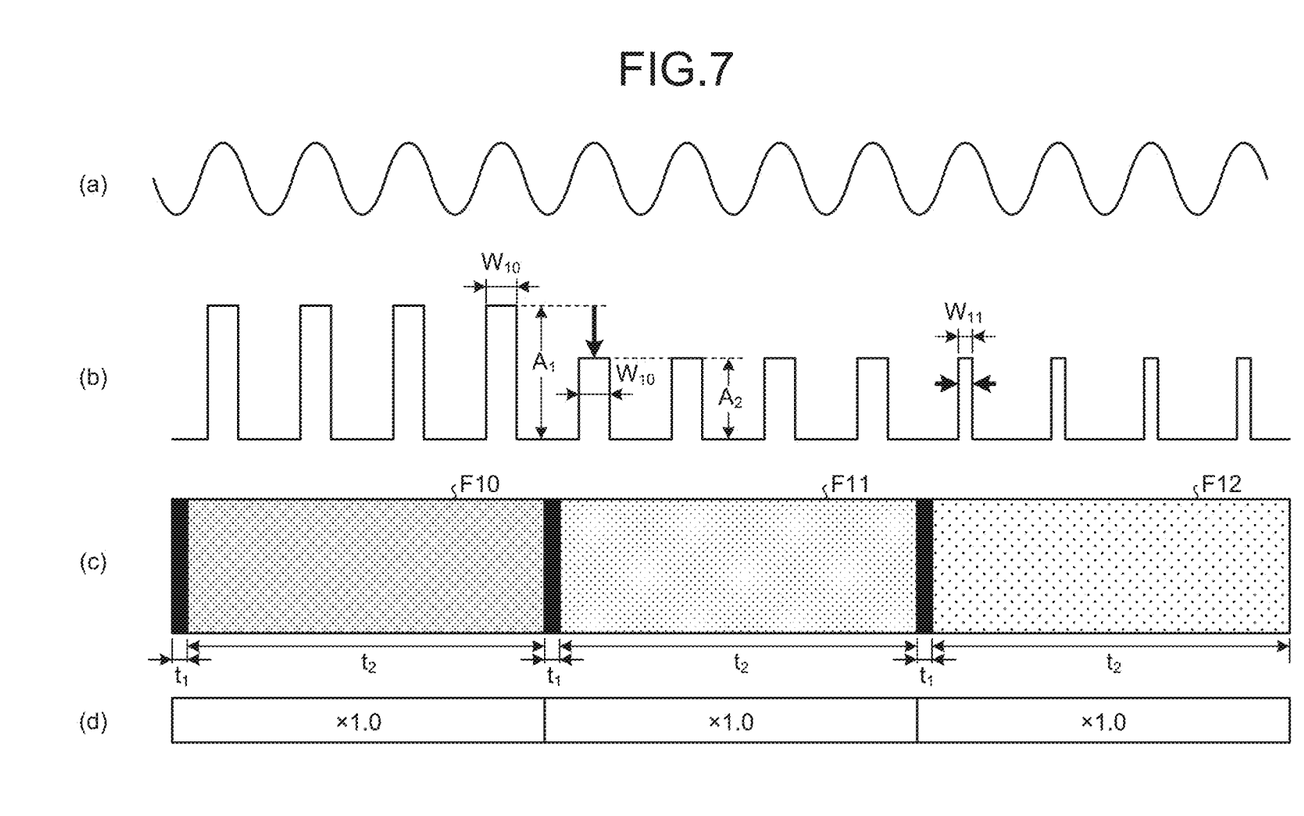
FIG. 7 is a diagram illustrating an overview of control by the control unit in a case where the vocal cord vibrational frequency is not equal to or greater than the threshold value.

FIG. 7 is a diagram illustrating an overview of control by the control unit 70 in a case where the vocal cord vibrational frequency is not equal to or greater than the threshold value. In FIG. 7, starting at the top, (a) illustrates the vocal cord vibrational frequency, (b) illustrates the light emission timing and intensity of the pulse light, (c) illustrates exposure frames of the image sensor 212, and (d) illustrates the gain which is applied to the image signal of the exposure frames by the AGC unit 64. Furthermore, the horizontal axis in (a) of FIG. 7 represents time and the vertical axis represents the phase state of vocal cord vibration, the horizontal axis in (b) of FIG. 7 represents time and the vertical axis represents intensity, the horizontal axis in (c) of FIG. 7 represents time, time $t_1$ represents timing for reading the image signal, and time $t_2$ represents exposure timing. In addition, frame F10 in (c) of FIG. 7 represents a frame (image signal) in which the image brightness is too bright, frame F11 represents a frame (image signal) for which a color temperature change is permissible, and frame F12 represents a frame (image signal) of appropriate brightness.

As illustrated in FIG. 7, first a case will be described where the control unit 70 controls the current value which the light source driving unit 61 supplies to the light source unit 60 to be within a permissible range (frame F11) for a color temperature change. In this case, the control unit 70 changes the light emission intensity from a light emission intensity $A_1$ to a light emission intensity $A_2$ by changing the current value which the light source driving unit 61 supplies to the light source unit 60, thereby performing dimming to the target value for the image brightness which has been input from the input device 3 (continuous dimming control). Specifically, the control unit 70 outputs, to the light source driving unit 61, a current value control signal that corresponds to the light emission intensity $A_2$ constituting the target value brightness. At such time, the light source driving unit 61 supplies a drive current (a pulse current) to the light source unit 60 in synchronization with the vocal cord vibrational frequency based on the PWM control signal and the current value control signal which are input from the control unit 70.

Subsequently, when the current value which the light source driving unit 61 supplies to the light source unit 60 is not within the permissible range for a color temperature change, the control unit 70 changes the pulse width of the pulse light emitted by the light source unit 60 from a pulse width $W_{10}$ to a pulse width $W_{11}$ in synchronization with the vocal cord frequency, in one frame period of the image sensor 212. Specifically, the control unit 70 outputs, to the light source driving unit 61, a PWM control signal whereby the pulse width of the pulse light emitted by the light source unit 60 is narrowed by being changed from a pulse width $W_{10}$ to a pulse width $W_{11}$ to achieve a target value brightness, based on the difference between a target value for the image brightness which is input from the input device 3 and the detection result of the brightness detection unit 63. At such time, the light source driving unit 61 supplies a drive current (a pulse current) to the light source unit 60 in synchronization with the vocal cord vibrational frequency based on the PWM control signal and the current value control signal which are input from the control unit 70. As a result, frame F12 has an appropriate brightness.

According to the second embodiment described hereinabove, it is possible to perform optimum strobe observation according to vocal cord frequency, wherein the control unit 70 determines whether or not the current value supplied to the light source unit 60 lies within the permissible range for an image color temperature change and, in a case where it is determined by the determination unit 68 that the vocal cord frequency is equal to or greater than the threshold value, the control unit 70 changes the current value supplied to the light source unit 60 when the current value supplied to the light source unit 60 lies within the range but changes the pulse-light light emission frequency in one frame period of the pulse light emitted by the light source unit 60 when the current value supplied to the light source unit 60 lies outside the range, and in a case where it is determined by the determination unit 68 that the vocal cord frequency is not equal to or greater than the threshold value, the light source unit 60 changes the current value supplied to the light source unit 60 when the current value supplied to the light source unit 60 lies within the range but changes the pulse width of the pulse light emitted by the light source unit 60 when the current value supplied to the light source unit 60 lies outside the range.

Furthermore, according to the second embodiment, as a result of the control unit 70 causing the AGC unit 64 to amplify the image signal of the latest frame F12, discontinuity in the brightness based on control of the pulse-light light emission frequency in one frame period may be absorbed, thereby enabling an image of appropriate brightness to be obtained.

Third Embodiment

A third embodiment will be described next. An endoscope system according to a third embodiment includes the same configurations as the endoscope system 1 according to the foregoing second embodiment and the processing executed is different. Specifically, in the foregoing second embodiment, in a case where the vocal cord vibrational frequency is equal to or greater than the threshold value, the light emission frequency of pulse light emission is changed when the current value which the light source driving unit 61 supplies to the light source unit 60 is not in the permissible range for a color temperature change, while gain adjustment is performed by the AGC unit 64, whereas, in the third embodiment, the pulse light emission frequency and the current value are changed. The processing executed by the endoscope system according to the third embodiment will be described hereinbelow. Note that the same reference signs are assigned to the same configurations as in the endoscope system 1 according to the foregoing second embodiment and that detailed descriptions of these configurations are omitted.

Endoscope System Processing

Figure 8:
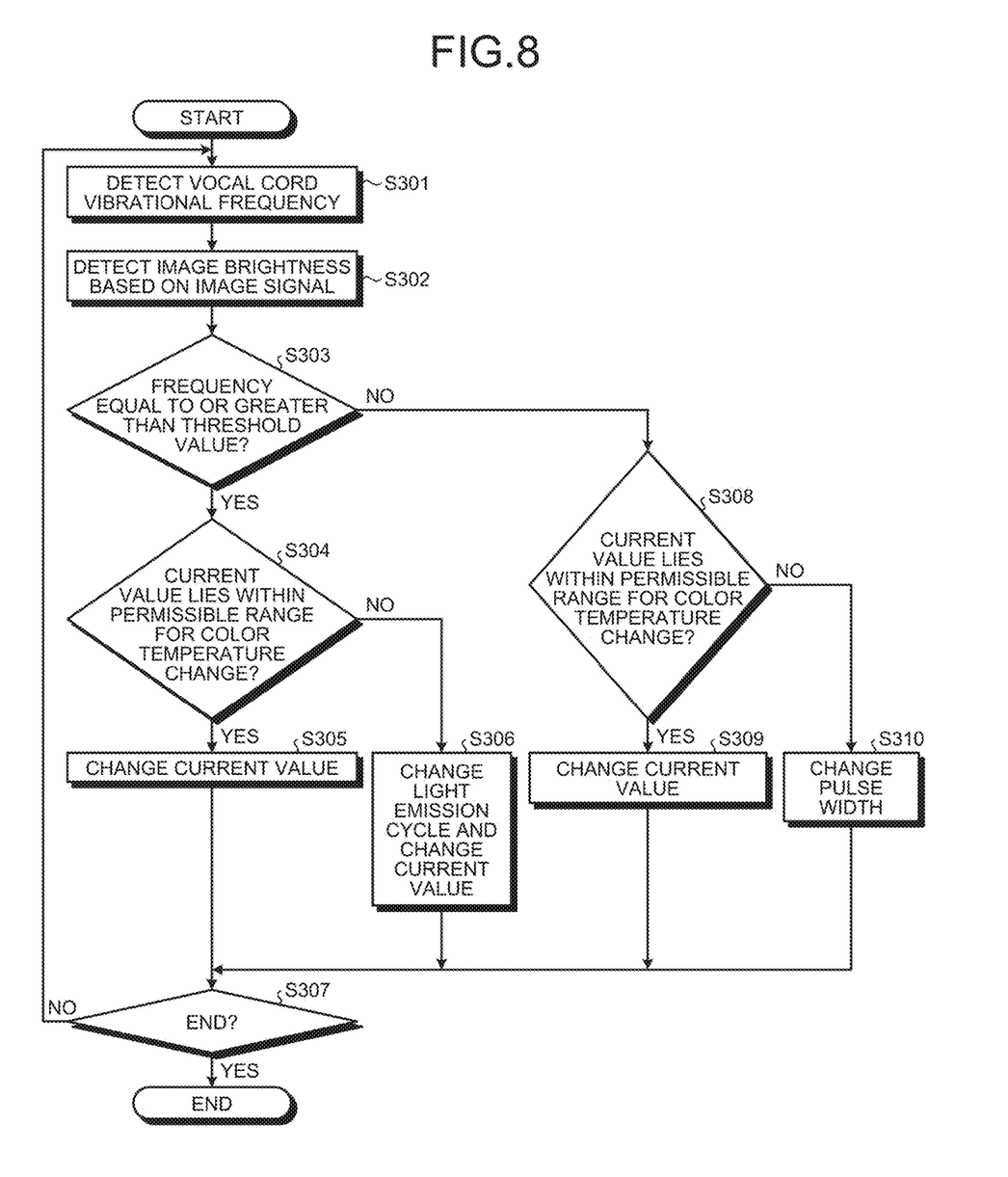
FIG. 8 is a flowchart illustrating an overview of processing executed by an endoscope system according to a third embodiment.

FIG. 8 is a flowchart illustrating an overview of processing executed by an endoscope system 1 according to the third embodiment. Steps S301 to S305 and steps S307 to S310 in FIG. 8 correspond to the foregoing steps S201 to S205 and steps S207 to S210, respectively, in FIG. 5, and only step S306 is different. Step S306 will be described hereinbelow.

In step S306, the control unit 70 changes the pulse-light light emission frequency in one frame period of the pulse light emitted by the light source unit 60 while changing to the current value for dimming to the target value for the image brightness which is input from the input device 3 by controlling the current value which the light source driving unit 61 supplies to the light source unit 60, based on a target value for the image brightness which is input from the input device 3, brightness information detected by the brightness detection unit 63, and the vocal cord frequency which is input from the vocal cord frequency detection unit 67. After step S306, the endoscope system 1 moves to step S307.

Figure 9:
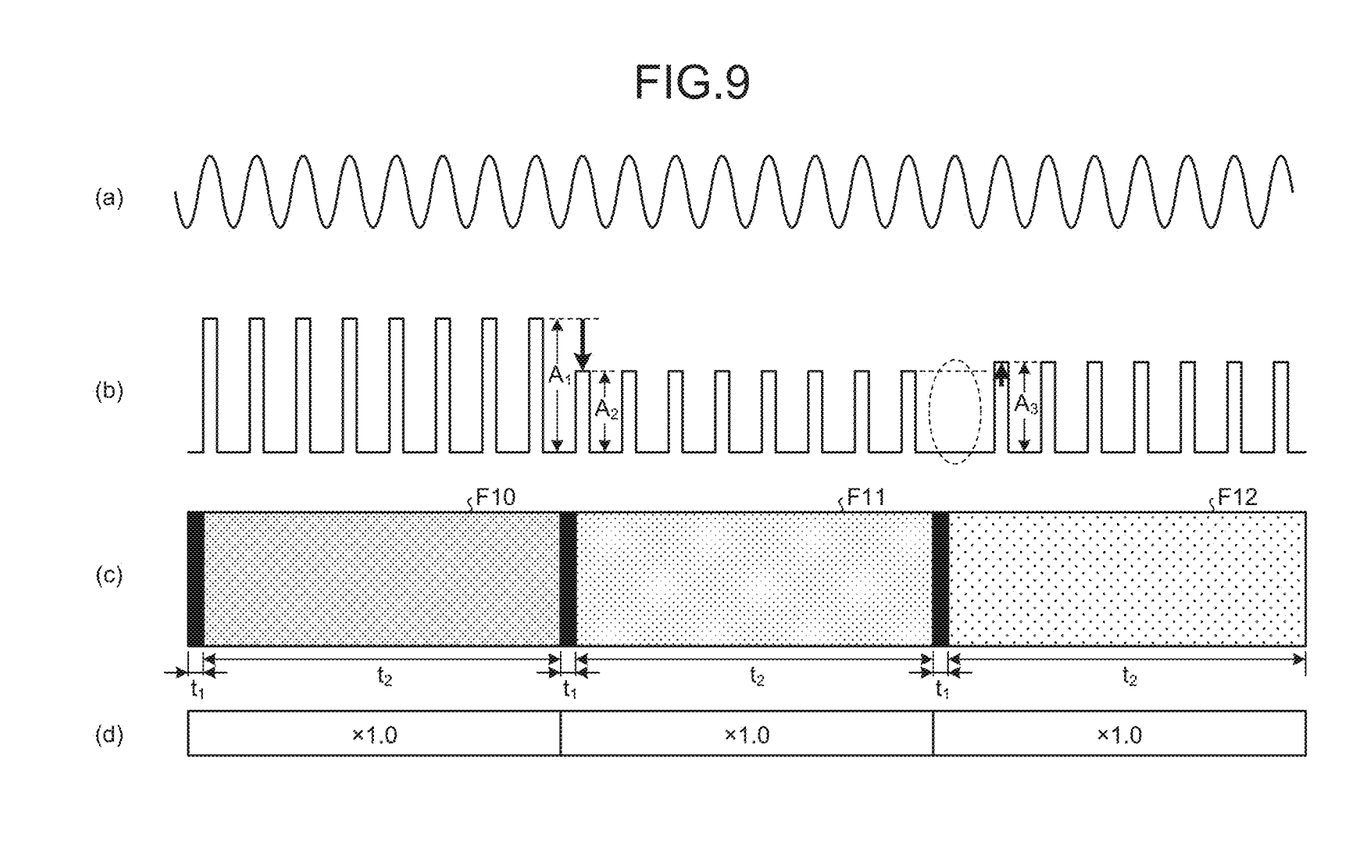
FIG. 9 is a diagram illustrating an overview of control by the control unit in a case where the vocal cord vibrational frequency is equal to or greater than a threshold value.

FIG. 9 is a diagram illustrating an overview of control by the control unit 70 in a case where the vocal cord vibrational frequency is equal to or greater than a threshold value. In FIG. 9, starting at the top, (a) illustrates the vocal cord vibrational frequency, (b) illustrates the light emission timing and intensity of the pulse light, (c) illustrates exposure frames of the image sensor 212, and (d) illustrates the gain which is applied to the image signal of the exposure frames by the AGC unit 64. Furthermore, the horizontal axis in (a) of FIG. 9 represents time and the vertical axis represents the phase state of vocal cord vibration, the horizontal axis in (b) of FIG. 9 represents time and the vertical axis represents intensity, the horizontal axis in (c) of FIG. 9 represents time, time $t_1$ represents timing for reading the image signal, and time $t_2$ represents exposure timing. In addition, frame F10 in (c) of FIG. 9 represents a frame (image signal) in which the image brightness is too bright, frame F11 represents a frame (image signal) for which a color temperature change is permissible, and frame F12 represents a frame (image signal) of appropriate brightness.

As illustrated in FIG. 9, when the current value which the light source driving unit 61 supplies to the light source unit 60 is not within a permissible range for a color temperature change, the control unit 70 changes the pulse-light light emission frequency in one frame by thinning the light emission frequency of the pulse light emitted by the light source unit 60 in synchronization with the vocal cord frequency, in one frame period of the image sensor 212. Furthermore, the control unit 70 changes the light emission intensity from a light emission intensity $A_2$ to a light emission intensity $A_3$ (light emission intensity $A_3$>light emission intensity $A_2$) by changing the current value which the light source driving unit 61 supplies to the light source unit 60, thereby performing dimming to the target value for the image brightness which has been input from the input device 3 (continuous dimming control). Specifically, the control unit 70 outputs, to the light source driving unit 61, a PWM control signal whereby the light emission frequency in one frame period in which the light source unit 60 emits pulse light is changed to achieve a target value brightness and a current value control signal that corresponds to the light emission intensity $A_3$, based on the difference between a target value for the image brightness which is input from the input device 3 and the detection result of the brightness detection unit 63. At such time, the light source driving unit 61 supplies a drive current (a pulse current) to the light source unit 60 in synchronization with the vocal cord vibrational frequency based on the PWM control signal and the current value control signal which are input from the control unit 70. As a result, frame F12 has an appropriate brightness.

According to the third embodiment described hereinabove, when the current value supplied to the light source unit 60 lies outside the range, the control unit 70 changes the pulse-light light emission frequency in one frame period of the pulse light emitted by the light source unit 60 while changing the current value supplied to the light source unit 60, and hence it is possible to absorb discontinuity in the brightness based on control of the pulse-light light emission frequency in one frame period, thereby enabling an image of appropriate brightness to be obtained.

FURTHER EMBODIMENTS

By suitably combining a plurality of constituent elements which are disclosed in the endoscope systems according to the foregoing first, second, and third embodiments of the present disclosure, various embodiments may be configured. For example, several constituent elements may be removed from among all the constituent elements disclosed in the endoscope systems according to the foregoing first, second, and third embodiments of the present disclosure. Moreover, the constituent elements described in the endoscope systems according to the foregoing first, second, and third embodiments of the present disclosure may also be suitably combined.

Furthermore, "parts" mentioned earlier in the endoscope systems according to the first, second, and third embodiments of the present disclosure may also be replaced with the wording "means" and "circuits", and so forth. For example, "control unit" may be replaced with "control means" or "control circuit".

In addition, a program that is executed by the endoscope systems according to the first, second, and third embodiments of the present disclosure is file data that is in an installable format or an executable format and that is provided by being recorded on a recording medium that is computer-readable, such as a CD-ROM, a flexible disk (FD), a CD-R, a digital versatile disk (DVD), a USB medium, or a flash memory.

Furthermore, a program that is executed by the endoscope systems according to the first, second, and third embodiments of the present disclosure may be configured to be stored on a computer connected to a network such as the internet or to be provided by being downloaded over the internet.

Note that, although expressions such as "first", "thereafter", and "next" are used in the flowchart descriptions in the present specification to illustrate the pre- and post-processing relationships between steps, the sequence of the processing for carrying out the present disclosure is not necessarily uniquely defined by such expressions. In other words, the sequence of the processing in the flowcharts disclosed in the present specification may be revised within a consistent scope.

The present disclosure exhibits an advantageous effect of making it possible to perform optimum strobe observation according to vocal cord frequency.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A light source control device to control a light source configured to intermittently emit pulse light, comprising:
    a processor comprising hardware, the processor being configured to
        detect a vocal cord vibrational frequency of a subject based on a voice signal input from an external device,
        determine whether or not the vocal cord frequency is equal to or greater than a threshold value,
        receive an image signal from an image sensor capturing reflected light from an object when the pulse light is projected onto the object,
        determine a difference between a target brightness and a brightness of the image signal, and
        on condition that the vocal cord frequency is equal to or greater than the threshold value, prohibit change in a pulse width of the pulse light and change a light emission frequency of the pulse light in one frame period of an image sensor of the pulse light emitted by the light source based on the difference, and
        on condition that the vocal cord frequency is not equal to or greater than the threshold value, prohibit change in the light emission frequency and change the pulse width of the pulse light emitted by the light source based on the difference.

2. The light source control device according to claim 1, wherein the threshold value is two times a frequency of a frame rate of the image sensor.

3. The light source control device according to claim 1, wherein the processor is configured to:
    change a current value supplied to the light source based on the difference;
    determine whether or not the current value supplied to the light source is within a permissible range for an image color temperature change;
    in a case where the vocal cord frequency is equal to or greater than the threshold value, change the current value when the current value is within the range, and change the light emission frequency when the current value is not within the range; and
    in a case where the vocal cord frequency is not equal to or greater than the threshold value, change the current value when the current value is within the range, and change the pulse width of the pulse light when the current value is not within the range.

4. The light source control device according to claim 3, further comprising:
    an autogain controller configured to adjust gain of the image signal, wherein
    the processor is configured to cause the autogain controller to amplify the image signal when the processor changes the light emission frequency.

5. The light source control device according to claim 3, wherein the processor is configured to change the light emission frequency while changing the current value.

6. A medical observation system comprising:
    the light source controlled by the light source control device according to claim 1;
    an endoscope including
        an insertable section configured to be inserted into a subject, and
        the image sensor configured to generate the image signal, the image sensor being disposed at an end portion of the insertable section; and
    a voice input device configured to receive a voice input and generate the voice signal, wherein
    the light source is configured to project the pulse light toward the object from the end portion by supplying pulse light to the endoscope.

7. The medical observation system according to claim 6, further comprising:
    an image processor configured to perform image processing on the image signal, wherein
    the processor is configured to output, to the image processor, light source information relating to the light emission frequency, the current value supplied to the light source, and the pulse width, and
    the image processor is configured to generate a display image displayed on a display device by performing image processing on the image signal based on the light source information.

8. The light source control device according to claim 1, wherein the changed light emission frequency of the pulsed light is constant.

9. The light source control device according to claim 8, wherein the changed pulse width of the pulsed light is constant.

10. The light source control device according to claim 1, wherein the changed pulse width of the pulsed light is constant.

11. A method of controlling a light source configured to intermittently emit pulse light, the method comprising:
- detecting a vocal cord vibrational frequency of a subject based on a voice signal;
- determining whether or not the vocal cord frequency is equal to or greater than a threshold value;
- receiving an image signal from an image sensor capturing reflected light from an object when the pulse light is projected onto the object;
- determining a difference between a target brightness and a brightness of the image signal;
- on condition that the vocal cord frequency is equal to or greater than the threshold value, prohibiting change in a pulse width of the pulse light and changing a light emission frequency of the pulse light in one frame period of an image sensor of the pulse light emitted by the light source based on the difference; and
- prohibiting change in the light emission frequency and changing the pulse width of the pulse light emitted by the light source based on the difference.

12. A non-transitory computer-readable recording medium on which an executable program is recorded, the program causing a processor of a light source control device including a light source configured to intermittently emit pulse light to execute:
- detecting a vocal cord vibrational frequency of a subject based on a voice signal;
- determining whether or not the vocal cord frequency is equal to or greater than a threshold value;
- receiving an image signal from an image sensor capturing reflected light from an object when the pulse light is projected onto the object;
- determining a difference between a target brightness and a brightness of the image signal;
- on condition that the vocal cord frequency is equal to or greater than the threshold value, prohibiting change in a pulse width of the pulse light and changing a light emission frequency of the pulse light in one frame period of an image sensor of the pulse light emitted by the light source based on the difference; and
- on condition that the vocal cord frequency is not equal to or greater than the threshold value, prohibiting change in the light emission frequency and changing the pulse width of the pulse light emitted by the light source based on the difference.

* * * * *